(12) United States Patent
Hermann et al.

(10) Patent No.: US 6,913,912 B2
(45) Date of Patent: Jul. 5, 2005

(54) PROCESS FOR THE PREPARATION OF D-PANTOTHENIC ACID AND/OR SALTS THEREOF

(75) Inventors: Thomas Hermann, Bielefeld (DE); Birgit Witteck, Dissen (DE); Mechthild Rieping, Bielefeld (DE)

(73) Assignee: Degussa AG, Hanau-Wolfgang (DE)

( * ) Notice: Subject to any disclaimer, the term of this patent is extended or adjusted under 35 U.S.C. 154(b) by 157 days.

(21) Appl. No.: 10/167,457

(22) Filed: Jun. 13, 2002

(65) Prior Publication Data

US 2003/0087404 A1 May 8, 2003

(30) Foreign Application Priority Data

Jun. 13, 2001 (DE) .......................................... 101 28 780

(51) Int. Cl.⁷ .............................. C12P 7/42; C12P 1/00; C12N 9/10; C12N 1/20; C07H 21/04
(52) U.S. Cl. ..................... 435/146; 435/41; 435/183; 435/193; 435/252.3; 435/252.32; 435/320.1; 530/350; 536/23.2
(58) Field of Search .................... 435/41, 106, 183, 435/193, 252.3, 252.32, 320.1; 530/350; 536/23.2

(56) References Cited

U.S. PATENT DOCUMENTS

| 5,518,906 A | 5/1996 | Hikichi et al. |
| 6,171,845 B1 | 1/2001 | Elischweski et al. |
| 6,238,714 B1 | 5/2001 | Binder et al. |

FOREIGN PATENT DOCUMENTS

| EP | 0 493 060 | 7/1992 |
| EP | 1001 027 | 5/2000 |
| EP | 1 050 219 | 11/2000 |
| WO | WO 96/33283 | 10/1996 |
| WO | WO 01/00843 | 1/2001 |
| WO | WO 02/101050 | 12/2002 |

OTHER PUBLICATIONS

M. Brune, et al., Nucleic Acids Research, vol. 13, No. 19, pp. 7139–7151, XP–001033922, "Cloning and Sequencing of the Adenylate Kinase Gene (ADK) of *Escherichia coli*", Oct. 11, 1995.

Blattner, et al., "The Complete Genome Sequence of *Escherichia coli* K–12", Science, vol. 277, Sep. 5, 1997, pp. 1453–1462.

Holmes, et al., "Purification and Characterization of Adenylate Kinase as an Apparent Adenosine Triphosphate–dependent Inhibitor of Ribonuclease II in *Escherichia coli*," The Journal of Biological Chemistry, vol. 248, No. 6, Mar. 25, 1973, pp. 2014–2021.

*Primary Examiner*—Manjunath N. Rao
*Assistant Examiner*—Christian L. Fronda
(74) *Attorney, Agent, or Firm*—Oblon, Spivak, McClelland, Maier & Neustadt, P.C.

(57) ABSTRACT

A process for the preparation of D-pantothenic acid and/or salts thereof or feedstuffs additives comprising these by fermentation of microorganisms of the Enterobacteriaceae family, in particular those which already produce D-pantothenic acid, in which the nucleotide sequence(s) in the microorganisms which code(s) for the adk gene is/are enhanced, in particular over-expressed.

27 Claims, 1 Drawing Sheet

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic DNA -continued

```
<400> SEQUENCE: 1
gcgggatccg gcaatcgcct gttggtggt                                     29

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA

<400> SEQUENCE: 2
acgggtcgac gtttgcttgt gcgggcctgt                                    30
```

PROCESS FOR THE PREPARATION OF D-PANTOTHENIC ACID AND/OR SALTS THEREOF

BACKGROUND OF THE INVENTION

1. Field of the Invention

The present invention relates to a process for the preparation of D-pantothenic acid and salts thereof or mixtures comprising these compounds using microorganisms of the Enterobacteriaceae family in which at least the adk gene is enhanced.

2. Description of the Background

Pantothenic acid is produced worldwide in an order of magnitude of several thousand tons a year. It is used inter alia in human medicine, in the pharmaceuticals industry and in the foodstuffs industry. A large portion of the pantothenic acid produced is used for nutrition of stock animals such as poultry and pigs.

Pantothenic acid can be prepared by chemical synthesis, or biotechnologically by fermentation of suitable microorganisms in suitable nutrient solutions. In the chemical synthesis, DL-pantolactone is an important precursor. It is prepared in a multi-stage process from formaldehyde, isobutylaldehyde and cyanide, and in further process steps, the racemic mixture is separated, D-pantolactone is subjected to a condensation reaction with β-alanine, and D-pantothenic acid is obtained in this way.

The typical commercial form is the calcium salt of D-pantothenic acid. The calcium salt of the racemic mixture of D,L-pantothenic acid is also customary.

The advantage of the fermentative preparation by microorganisms lies in the direct formation of the desired stereoisomeric form, that is to say the D-form, which is free from L-pantothenic acid.

Various types of bacteria, such as e.g. *Escherichia coli* (*E. coli*), *Arthrobacter ureafaciens, Corynebacterium erythrogenes, Brevibacterium ammoniagenes*, and also yeasts, such as e.g. *Debaromyces castellii*, can produce D-pantothenic acid in a nutrient solution which comprises glucose, DL-pantoic acid and β-alanine, as shown in EP-A 0 493 060. EP-A 0 493 060 furthermore shows that in the case of *E. coli*, the formation of D-pantothenic acid is improved by amplification of pantothenic acid biosynthesis genes from *E. coli* which are contained on the plasmids pFV3 and pFV5 in a nutrient solution comprising glucose, DL-pantoic acid and β-alanine.

EP-A 0 590 857 and U.S. Pat. No. 5,518,906 describe mutants derived from *E. coli* strain IFO3547, such as FV5714, FV525, FV814, FV521, FV221, FV6051 and FV5069, which carry resistances to various antimetabolites, such as salicylic acid, α-ketobutyric acid, β-hydroxyaspartic acid, O-methylthreonine and α-ketoisovaleric acid. They produce pantoic acid in a nutrient solution comprising glucose, and D-pantothenic acid in a nutrient solution comprising glucose and β-alanine. It is furthermore stated in EP-A 0 590 857 and U.S. Pat. No. 5,518,906 that after amplification of the pantothenic acid biosynthesis genes panB, panC and panD, which are said to be contained on the plasmid pFV31, in the above-mentioned strains the production of D-pantoic acid in nutrient solutions comprising glucose and the production of D-pantothenic acid in a nutrient solution comprising glucose and β-alanine is improved.

WO 97/10340 furthermore reports on the favorable effect of the enhancement of the ilvGM operon on the production of D-pantothenic acid. Finally, EP-A-1001027 reports on the effect of the enhancement of the panE gene on the formation of D-pantothenic acid.

According to known procedures, the D-pantothenic acid or the corresponding salt is isolated from the fermentation broth and purified (EP-A-0590857 and WO 96/33283) and used accordingly in purified form, or the fermentation broth comprising D-pantothenic acid is dried in total (EP-A-1050219) and used in particular as a feedstuffs additive.

SUMMARY OF THE INVENTION

It is an object of the invention to provide new methods for improved fermentative preparation of D-pantothenic acid and/or salts thereof, and animal feedstuffs additives comprising these compounds.

The invention provides a process for the preparation of D-pantothenic acid and/or salts thereof using microorganisms of the Enterobacteriaceae family which in particular already produce D-pantothenic acid and in which at least one, preferably endogenous nucleotide sequence(s) which code(s) for the adk gene is enhanced, in particular over-expressed.

In particular, the process is characterized in that the following steps are carried out:

a) fermentation of microorganisms of the Enterobacteriaceae family which produce D-pantothenic acid and in which at least the adk gene is enhanced, in particular over-expressed; the gene which codes for adenylate kinase and optionally alleles of this gene are enhanced, in particular over-expressed, under conditions suitable for the formation of the gene product; further genes of the pantothenic acid biosynthesis pathway are optionally attenuated or enhanced at the same time in order to increase the production of pantothenic acid;

b) the fermentation is optionally carried out in the presence of alkaline earth metal compounds, these being added to the fermentation broth continuously or discontinuously in preferably stoichiometric amounts;

c) concentration of the D-pantothenic acid or the corresponding salts in the medium or the fermentation broth or optionally in the cells of the microorganisms of the Enterobacteriaceae family, and d) after conclusion of the fermentation, isolation of the D-pantothenic acid, and/or of the corresponding salt(s).

The invention also provides a process in which, after conclusion of the fermentation, some or all ($\geq 0$ to 100%) of the biomass remains in the fermentation broth, and the broth obtained in this way is processed, optionally after concentration, to a solid mixture which comprises D-pantothenic acid and/or salts thereof and preferably comprises further constituents from the fermentation broth.

These further constituents are, above all, the dissolved compounds which originate from the feed medium and soluble organic compounds which are formed.

A more complete appreciation of the invention and many of the attendant advantages thereof will be readily obtained as the same becomes better understood by reference to the following Figures in conjunction with the detailed description below.

Figure 1:
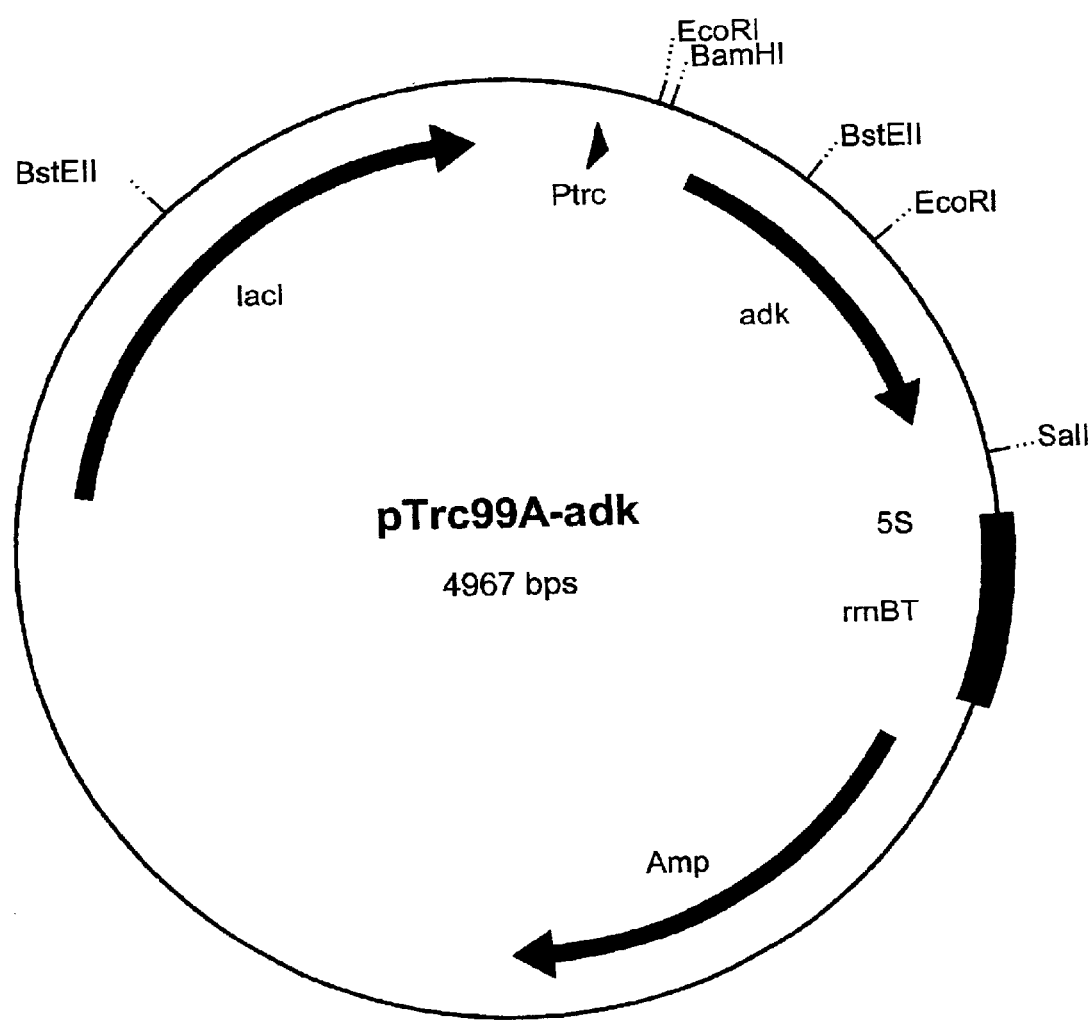
FIG. 1: Map of the plasmid pTrc99A-adk containing the adk gene.

The length data are to be understood as approx. data. The abbreviations and designations used have the following meaning:

Amp: Ampicillin resistance gene lacI: Gene for the repressor protein of the trc promoter Ptrc: trc promoter region, IPTG-inducible adk: Coding region of the adk gene 5S: 5S rRNA region rrnBT: rRNA terminator region bps Base pairs The abbreviations for the restriction enzymes have the following meaning:

BamHI: Restriction endonuclease from *Bacillus amyloliquefaciens*

BstEII: Restriction endonuclease from *Bacillus stearothermophilus ET*

EcoRI: Restriction endonuclease from *Escherichia coli*

SalI: Restriction endonuclease from *Streptomyces albus*

DETAILED DESCRIPTION OF THE INVENTION

When D-pantothenic acid or pantothenic acid or pantothenate are mentioned in the following text, this means not only the free acids but also the salts of D-pantothenic acid, such as e.g. the calcium, sodium, ammonium or potassium salt.

"Endogenous genes" or "endogenous nucleotide sequences" are understood as meaning the genes or nucleotide sequences present in the population of a species.

The term "enhancement" in this connection describes the increase in the intracellular activity of one or more enzymes or proteins in a microorganism which are coded by the corresponding DNA, for example by increasing the number of copies of the gene or genes, of the ORF (Open Reading Frame) or ORFs, using a potent promoter or a gene or allele or ORF which codes for a corresponding enzyme or protein with a high activity, and optionally combining these measures.

By enhancement measures, in particular over-expression, the activity or concentration of the corresponding enzyme or protein is in general increased by at least 10%, 25%, 50%, 75%, 100%, 150%, 200%, 300%, 400% or 500%, up to a maximum of 1000% or 2000%, based on that of the wild-type protein or wild-type enzyme or the activity or concentration of the protein or enzyme in the starting microorganism.

The microorganisms which the present invention provides can produce D-pantothenic acid from glucose, sucrose, lactose, fructose, maltose, molasses, starch, cellulose or from glycerol and ethanol. They are representatives of Enterobacteriaceae, in particular of the genus *Escherichia*. Of the genus *Escherichia*, the specie *Escherichia coli* is to be mentioned in particular. Within the species *Escherichia coli* the so-called K-12 strains, such as e.g. the strains MG1655 or W3110 (Neidhard et al.: *Escherichia coli* and *Salmonella*. Cellular and Molecular Biology (ASM Press, Washington D.C.)) or the *Escherichia coli* wild type strain IFO3547 (Institute of Fermentation, Osaka, Japan) and mutants derived from these which have the ability to produce D-pantothenic acid are suitable.

Suitable D-pantothenic acid-producing strains of the genus *Escherichia*, in particular of the species *Escherichia coli*, are, for example

*Escherichia coli* FV5069/pFV31

*Escherichia coli* FV5069/pFV202

*Escherichia coli* FE6/pFE80 and

*Escherichia coli* KE3

It has been found that Enterobacteriaceae produce D-pantothenic acid in an improved manner after enhancement, in particular over-expression of the adk gene. The use of endogenous genes is preferred.

The nucleotide sequences of the genes or open reading frames (ORF) of *Eecherichia coli* are known, and can also be found in the genome sequence of *Eecherichia coli* published by Blattner et al. (Science 277, 1453–1462 (1997)).

The following information, inter alia, on the adk gene can be found in the following:

| | |
|---|---|
| Description: | Adenylate kinase |
| Alternative gene names: | plsA, dnaW |
| EC No.: | 2.7.4.3 |
| Reference: | Brune et al., Nucleic Acids Research 13: 7139–7151 (1985), Holmes and Singer, Journal of Biological Chemistry. 248(6): 2014–2021 (1973) |
| Accession No.: | AE000153 |

The gene described in the reference cited above can be used according to the invention. Alleles of the gene or open reading frames which result from the degeneracy of the genetic code or due to sense mutations of neutral function can furthermore be used, the activity of the proteins being substantially unchanged.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative D-pantothenic acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by one skilled in the art, inter alia, in Chang and Cohen (Journal of Bacteriology 134:1141–1156 (1978)), in Hartley and Gregori (Gene 13:347–353 (1981)), in Amann and Brosius (Gene 40:183–190 (1985)), in de Broer et al. (Proceedings of the National Academy of Sciences of the United States of America 80:21–25 (1983)), in LaVallie et al. (BIO/TECHNOLOGY 11, 187–193 (1993)), in PCT/US97/13359, in Llosa et al. (Plasmid 26:222–224 (1991)), in Quandt and Klipp (Gene 80:161–169 (1989)), in Hamilton (Journal of Bacteriology 171:4617–622 (1989), in Jensen and Hammer (Biotechnology and Bioengineering 58, 191–195 (1998) and in known textbooks of genetics and molecular biology.

Plasmid vectors which are capable of replication in Enterobacteriaceae, such as e.g. cloning vectors derived from pACYC184 (Bartolomé et al.; Gene 102, 75–78 (1991)), pTrc99A (Amann et al.; (Gene 69:301–315 (1988)) or pSC101 derivatives (Vocke and Bastia, Proceedings of the National Academy of Science USA 80 (21):6557–6561 (1983)) can be used. A strain transformed with one or more plasmid vectors where the plasmid vector(s) carries at least one nucleotide sequence which codes for the adk gene can be employed in a process according to the invention.

It may furthermore be advantageous for the production of D-pantothenic acid with strains of the Enterobacteriaceae family, in addition to the enhancement of the adk gene, for one or more of the genes chosen from the group consisting of the ilvGM operon which codes for acetohydroxy-acid synthase II (WO97/10340), the panB gene which codes for ketopantoate hydroxymethyl transferase (U.S. Pat. No. 5,518,906), the panE gene which codes for ketopantoate reductase (EP-A-1001027), the panD gene which codes for aspartate decarboxylase (U.S. Pat. No. 5,518,906), the panC gene which codes for pantothenate synthetase (U.S. Pat. No. 5,518,906), the glyA gene which codes for serine hydroxymethyl transferase (Plamann et al., Nucleic Acids Research 11(7):2065–2075(1983)), the genes gcvT, gcvH and gcvP which code for the glycine cleavage system (Okamura-Ikeda et al., European Journal of Biochemistry 216, 539–548 (1993)), the serA gene which codes for phosphoglyceric acid dehydrogenase (Tobey und Grant, Journal of Biological Chemistry 261:12179–12183(1986)), the serA(FBR) allele which codes for "feed back" resistant variants of phosphoglyceric acid dehydrogenase (DE-A-4232468), the serC gene which codes for phosphoserine transaminase (Duncan und Coggins, Biochemical Journal 234:49–57 (1986)), the bfr gene which codes for bacterioferrin (Andrews et al., Journal of Bacteriology 171:3940–3947 (1989)), the hns gene which codes for the DNA-binding protein HLP-II (reference: Pon et al., Molecular and General Genetics 212:199–202 (1988)), the pgm gene which codes for phosphoglucomutase (Lu and Kleckner, Journal of Bacteriology 176:5847–5851 (1994)), the mdh gene which codes for malate dehydrogenase (Sutherland und McAlister-Henn, Journal of Bacteriology 1985 163:1074–1079 (1985)), the cysK gene which codes for cysteine synthase A (Boronat et al., Journal of General Microbiology 130:673–685 (1984)), the fda gene which codes for fructose bisphosphate aldolase (class II) (Alefounder et al., Biochemical Journal 257:529–534 (1989)), the dldH gene which codes for NADH-dependent lipoamide dehydrogenase (reference: Stephens et al., European Journal of Biochemistry 135:519–527 (1983)), the pepB gene which codes for peptidase B (Hermsdorf et al., International Journal of Peptide and Protein Research 13:146–151 (1979); Suzuki et al., Journal of Fermentation and Bioengineering 82:392–397 (1996); Suzuki et at., Journal of Bacteriology 183(4): 1489–1490, (2001)) and the aldH gene which codes for NADP-dependent aldehyde dehydrogenase (Heim and Strehler, Gene 99:15–23 (1991)) to be enhanced, in particular overexpressed, individually or together. The use of endogenous genes is preferred.

Finally, it may be advantageous for the production of D-pantothenic acid with strains of the Enterobacteriaceae family, in addition to the enhancement of the adk gene, for one or more of the genes chosen from the group consisting of the avtA gene which codes for transaminase C (EP-A-1001027)

the poxB gene which codes for pyruvate oxidase (Grabau and Cronan, Nucleic Acids Research. 14 (13), 5449–5460 (1986))

the pckA gene which codes for PEP carboxykinase (Medina et al., Journal of Bacteriology 172, 7151–7156 (1990))

to be attenuated, in particular eliminated or expressed at a low level, individually or together.

The term "attenuation" in this connection describes the reduction or elimination of the intracellular activity of one or more enzymes or proteins in a microorganism which are coded by the corresponding DNA, for example by using a weak promoter or using a gene or allele which codes for a corresponding enzyme or protein with a low activity or inactivates the corresponding gene or enzyme (protein), and optionally combining these measures.

By attenuation measures, including reduction in expression, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

In addition to over-expression of the adk gene it may furthermore be advantageous for the production of D-pantothenic acid to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982). Bacteria in which the metabolic pathways which reduce the formation of D-pantothenic acid are at least partly eliminated can be employed in the process according to the invention.

The microorganisms produced according to the invention can be cultured in the batch process (batch culture), the fed batch (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Precursors of pantothenic acid, such as aspartate, β-alanine, ketoisovalerate, ketopantoic acid or pantoic acid and optionally salts thereof, can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture.

For the preparation of alkaline earth metal salts of pantothenic acid, in particular the calcium salt or magnesium salt, it is equally possible to add the suspension or solution of an inorganic compound containing an alkaline earth metal, such as, for example, calcium hydroxide or MgO, or of an organic compound, such as the alkaline earth metal salt of an organic acid, for example calcium acetate, continuously or discontinuously during the fermentation. For this purpose, the cation necessary for preparation of the desired alkaline earth metal salt of D-pantothenic acid is introduced into the fermentation broth directly in the desired amount, preferably in an amount of 0.95 to 1.1 equivalents.

However, the salts can also be formed after conclusion of the fermentation by addition of the inorganic or organic compounds to the fermentation broth, from which the biomass has optionally been removed beforehand.

Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. The pH is in general between 5.0 to 8.0, preferably 5.5 to 7.6. The fermentation is continued until a maximum of D-pantothenic acid has formed. This target is usually reached within 10 hours to 160 hours.

The D-pantothenic acid or the corresponding salts of D-pantothenic acid contained in the fermentation broth can then be isolated and purified in accordance with known procedures.

It is also possible for the fermentation broths comprising D-pantothenic acid and/or salts thereof preferably first to be freed from all or some of the biomass by known separation methods, such as, for example, centrifugation, filtration, decanting or a combination thereof. However, it is also possible to leave the biomass in its entirety in the fermentation broth. In general, the suspension or solution is preferably concentrated and then worked up to a powder, for example with the aid of a spray dryer or a freeze-drying unit. This powder is then in general converted by suitable compacting or granulating processes, e. g. also build-up granulation, into a coarser-grained, free-flowing, storable and largely dust-free product with a particle size distribution of preferably 20 to 2000 µm, in particular 100 to 1400 µm. In the granulation or compacting it is advantageous to employ conventional organic or inorganic auxiliary substances or carriers, such as starch, gelatine, cellulose derivatives or similar substances, such as are conventionally used as binders, gelling agents or thickeners in foodstuffs or feedstuffs processing, or further substances, such as, for example, silicas, silicates or stearates.

Alternatively, the fermentation product, with or without further of the conventional fermentation constituents, can be absorbed, in particular sprayed, on to an organic or inorganic carrier substance which is known and conventional in feedstuffs processing, such as, for example, silicas, silicates, grits, brans, meals, starches, sugars or others, and/or stabilized with conventional thickeners or binders. Use examples and processes in this context are described in the literature (Die Mühle+Mischfuttertechnik 132 (1995) 49, page 817).

These mixtures comprising the carrier substances can also be processed to a product with the desired particle size distribution by granulation processes.

D-Pantothenic acid and/or the desired salt of D-pantothenic acid or a formulation comprising these compounds is optionally added in a suitable process stage during or after the fermentation in order to achieve or establish the content of pantothenic acid desired in the product or the desired salt.

The desired content of pantothenic acid and/or the desired salt is in general in the range from 20 to 80 wt. % (based on the dry weight).

The concentration of pantothenic acid can be determined with known chemical (Velisek; Chromatographic Science 60, 515–560 (1992)) or microbiological methods, such as e.g. the Lactobacillus plantarum test (DIFCO MANUAL, $10^{th}$ Edition, p. 1100–1102; Michigan, USA).

The present invention is explained in more detail in the following with the aid of embodiment examples.

The minimal (M9) and complete media (LB) for *Eecherichia coli* used are described by J. H. Miller (A Short Course in Bacterial Genetics (1992), Cold Spring Harbor Laboratory Press). The isolation of plasmid DNA from *Escherichia coli* and all techniques of restriction, ligation, Klenow and alkaline phosphatase treatment are carried out by the method of Sambrook et al. (Molecular cloning—A laboratory manual (1989), Cold Spring Harbor Laboratory Press). The transformation of *Escherichia coli* is carried out by the method of Chung et al. (Proceedings of the National Academy of Sciences of the United States of America (1989) 86: 2172–2175) or by the method of Chuang et. al. (Nucleic Acids Research (1995) 23: 1641).

EXAMPLES

Having generally described this invention, a further understanding can be obtained by reference to certain specific examples which are provided herein for purposes of illustration only and are not intended to be limiting unless otherwise specified.

Example 1

Construction of the Expression Plasmid pTrc99A-adk

The adk gene from *E. coli* K12 is amplified using the polymerase chain reaction (PCR) and synthetic oligonucleotides. Starting from the nucleotide sequence of the adk gene in *E. coli* K12 MG1655 (Accession Number AE000153, Blattner et al. (Science 277, 1453–1462 (1997)), PCR primers are synthesized (MWG Biotech, Ebersberg, Germany). The 5' ends of the primers are lengthened with recognition sequences for restriction enzymes and two to four additional bases. This part of the primer is identified in the following description by a hyphen (-). The recognition sequence for BamHI is chosen for the 5' primer and the recognition sequence for SalI for the 3' primer, which are marked by underlining in the nucleotide sequence shown below:

```
Primer adk5':
5'-GCGGGATCC-GGCAATCGCCTGTTGGTGGT-3'    (SEQ ID No.1)

Primer adk3':
5'-ACGGGTCGAC-GTTTGCTTGTGCGGGCCTGT-3'    (SEQ ID No.2)
```

The chromosomal *E. coli* K12 MG1655 DNA employed for the PCR is isolated according to the manufacturer's instructions with "Qiagen Genomic-tips 100/G" (QIAGEN, Hilden, Germany). A DNA fragment approx. 800 bp in size can be amplified with the specific primers under standard PCR conditions (Innis et al. (1990) PCR Protocols. A Guide to Methods and Applications, Academic Press) with Pfu-DNA polymerase (Promega Corporation, Madison, USA). The PCR product is ligated according to the manufacturer's instructions with the vector pCR-Blunt II-TOPO (Zero Blunt TOPO PCR Cloning Kit, Invitrogen, Groningen, The Netherlands) and transformed into the E. coli strain TOP10. Selection of plasmid-carrying cells takes place on LB agar, to which 50 µg/ml kanamycin are added. After isolation of the plasmid DNA, the vector pCR-Blunt II-TOPO-adk is cleaved with the restriction enzymes BamHI and SalI and, after separation in 0.8% agarose gel, the adk fragment is isolated with the aid of the QIAquick Gel Extraction Kit (QIAGEN, Hilden, Germany). The vector pTrc99A (Amersham Biosciences, Freiburg, Germany) is cleaved with the enzymes BamHI and SalI, subsequently dephosphorylated with alkaline phosphatase according to the manufacturer's instructions (Amersham Biosciences, Freiburg, Germany) and ligated with the adk fragment isolated. The E. coli strain XL1-Blue MRF' (Stratagene, La Jolla, USA) is transformed with the ligation batch and plasmid-carrying cells are selected on LB agar, to which 50 µg/ml ampicillin is added. Successful cloning can be demonstrated after plasmid DNA isolation by control cleavage with the enzymes BamHI and SalI, EcoRI and BstEII. The plasmid is called pTrc99A-adk (FIG. 1).

Example 2

Preparation of the Strains FE6-1/pTrc99A and FE6-1/pTrc99A-adk

The E. coli strain FE6 is a valine-resistant mutant of E. coli K12 MG1655 (U.S. Pat. No. 6,171,845) and is deposited as DSM12379 at the Deutsche Sammlung für Mikroorganismen und Zellkulturen (DSMZ=German Collection of Microorganisms and Cell Cultures, Braunschweig, Germany). Starting from FE6, after incubation at 37° C. on minimal agar, to which 2 g/L glucose and 1 g/L β-hydroxyaspartic acid are added, spontaneous mutants are isolated. A selected β-hydroxyaspartic acid-resistant individual colony is then incubated on minimal agar, which comprises 2 g/L glucose and 0.2 g/L O-methylthreonine, at 37° C. After this step, a mutant called FE6–1 is resistant to L-valines, α-ketoisovaleric acid, β-hydroxyaspartic acid and O-methylthreonine. A pure culture of the strain FE6–1 was deposited on 8th, Sep. 2000 as DSM13721 at the Deutsche Sammlung für Mikroorganismen und Zellkulturen (DSMZ=German Collection of Microorganisms and Cell Cultures, Braunschweig, Germany).

The plasmids pTrc99A and pTrc99A-adk are transformed individually into the strain FE6–1 and plasmid-carrying cells are selected on LB agar, to which 50 µg/ml ampicillin are added. The strains obtained are called FE6-1/pTrc99A and FE6-1/pTrc99A-adk.

Example 3

Preparation of D-pantothenic acid with Strains Derived from FE6-1

The pantothenate production of the E. coli strains FE6-1/pTrc99A and FE6-1/pTrc99A-adk is checked in batch cultures of 10 ml contained in 100 ml conical flasks. For this, 10 ml of preculture medium of the following composition: 2 g/l yeast extract, 10 g/l $(NH_4)_2SO_4$, 1 g/l $KH_2PO_4$, 0,5 g/l $MgSO_4*7H_2O$, 15 g/l $CaCO_3$, 20 g/l glucose, 50 mg/l ampicillin are inoculated with an individual colony and incubated for 20 hours at 33° C. and 200 rpm on an ESR incubator from Kühner AG (Birsfelden, Switzerland). In each case 200 µl of this preculture are transinoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose, 20 g/l β-alanine, 250 mg/l thiamine) and the batch is incubated for 48 hours at 37° C. After the incubation the optical density (OD) of the culture suspension is determined with an LP2W photometer from Dr. Lange (Düsseldorf, Germany) at a measurement wavelength of 660 nm.

The concentration of the D-pantothenate formed is then determined in the culture supernatant centrifuged off by means of High Performance Liquid Chromatography [column: Reversed Phase MZ-Aqua Perfect (diameter 4,6 mm), mobile Phase 25 mM acetate buffer with 10% methanol, flow rate 1 ml/min, RI detector].

The result of the experiment is shown in Table 1.

TABLE 1

| Strain | OD (660 nm) | Pantothenate mg/l |
|---|---|---|
| FE6-1/pTrc99A | 8.7 | 47 |
| FE6-1/pTrc99A-adk | 9.1 | 54 |

The publications cited in the detailed description of the Invention and the Examples above are incorporated herein by reference.

Obviously, numerous modifications and variations of the present invention are possible in light of the above teachings. It is therefore to be understood that within the scope of the appended claims, the invention may be practiced otherwise than as specifically described herein.

This application is based on German Patent Application Ser. No. 101 28 780.1, filed on Jun. 13, 2001, and incorporated herein by reference.

What is claimed is:

1. A process for the preparation of D-pantothenic acid and/or salt thereof comprising: culturing an isolated or purified modified microorganism of Eseherichia coli for a time and under conditions suitable for production of D-pantothenic acid or a salt of D-pantothenic acid, and recovering D-pantothenic acid and/or salt of D-pantothenic acid;

wherein said modified microorganism has been transformed with a polynucleotide encoding Escherichia coli adenylate kinase and wherein said modified microorganism expresses an increased amount of adenylate kinase compared to the unmodified starting strain, and wherein said polynucleotide encoding adenylate kinase comprises a polynucleotide sequence (i) obtained by PCR amplification of chromosomal DNA from Escherichia coli using primers adk5' (SEQ ID NO: 1) and adk3' (SEQ ID NO: 2) or (ii) which has exactly the same polynucleotide sequence as a polynucleotide encoding Escherichia coli adenylate kinase which is obtained by PCR amplification of chromosomal DNA from Eseherichia coli using primers adk5' (SEQ ID NO: 1) and adk3'(SEQ ID NO: 2).

2. The process of claim 1, wherein said modified microorganism a contains said polynucleotide encoding Eseherichia coli adenylate kinase at a higher copy number than the unmodified starting strain.

3. The process of claim 1, wherein the expression of said polynucleotide encoding Escherichia coli adenylate kinase in said modified microorganism has been increased by modifying the promoter or regulatory region of said polynucleotide encoding Escherichia coli adenylate kinase compared to the unmodified starting strain.

4. The process of claim 1, wherein the expression of said polynucleotide encoding Escherichia coli adenylate kinase in said modified microorganism has been increased by prolonging the half-life of the mRNA encoding adenylate kinase.

5. The process of claim 1, wherein the D-pantothenic acid and/or a D-pantothenic acid salt is recovered as a composition suitable for use as a feedstuff additive.

6. The process of claim 1, further comprising isolating or purifying the D-pantothenic acid and/or a D-pantothenic acid salt.

7. The process of claim 1, wherein said pantothenic acid or salt of pantothenic acid is recovered as a fermentation broth.

8. The process of claim 1, wherein said pantothenic acid or salt of pantothenic acid is recovered from the fermentation broth after removal of some or all of the biomass.

9. The process of claim 1, wherein said modified microorganism further expresses an increased amount of the product(s) of one or more of the following gene(s) compared to the unmodified starting strain: ilvGM operon (acetohydroxy-acid transferase), panB (ketopantoate hydroxymethyl transferase), panC (pantothenate synthetase), panD (aspartate decarboxylase), panE (ketopantoate reductase), glyA (serine hydroxymethyl transferase), gcvT/gcvH/gcvP (glycine cleavage system), serA (phosphoglyceric acid dehydrogenase), serA(FBR) (feed-back resistant variants of phosphoglyceric acid dehydrogenase), serC (phophoserine transaminase), bfr (bacterioferrin), hns (DNA-binding protein HLP-II), pgm (phosphoglucomutase), mdh (malate dehydrogenase), cysK (cysteine synthase A), fda (fructose bisphosphate aldolase-class II), dldH (NADH-dependent lipoamide dehydrogenase), pepB (peptidase), or aldH (aldehyde dehydrogenase).

10. The process of claim 1, wherein said modified microorganism further expresses a decreased amount of the product(s) of one or more of the following gene(s) compared to the unmodified starting strain: avtA (transaminase C), poxB (pyruvate oxidase) or pckA (PEP carboxykinase).

11. The process of claim 1, wherein said microorganism is cultured in a batch process.

12. The process of claim 1, wherein said microorganism is cultured in a fed batch process.

13. The process of claim 1, wherein said microorganism is cultured in a repeated fed batch process.

14. The process of claim 1, wherein an alkaline earth metal is added to the fermentation broth continuously or discontinuously during fermentation in an amount ranging from 0.95 to 1.1 equivalents.

15. The process of claim 1, wherein calcium is added to the fermentation broth continuously or discontinuously during fermentation in an amount ranging from 0.95 to 1.1 equivalents.

16. The process of claim 1, wherein magnesium is added to the fermentation broth continuously or discontinuously during fermentation in an amount ranging from 0.95 to 1.1 equivalents.

17. The process of claim 1, further comprising absorbing the fermentation product onto a feedstuff carrier.

18. The process of claim 17, wherein said carrier is a silica(s) or silicate(s).

19. The process of claim 17, wherein said carrier comprises at least one ingredient selected from the group consisting of grit(s), bran(s), meal(s), starch(es), or sugar(s).

20. The process of claim 1, wherein recovering of D-pantothenic acid and/or a salt thereof comprises:
   a) separating some or all of the biomass from the fermentation broth obtained by the process of claim 1 to form a solution or suspension, and
   b) converting said solution or suspension into a powder or granule with a particle size distribution ranging from 20 to 2,000 μm.

21. The process of claim 20, wherein said particle size distribution ranges from 100 to 1,400 μm.

22. The process of claim 20, further comprising adding D-pantothenic acid and/or a salt thereof to said solution or suspension.

23. The process of claim 20, further comprising adding a conventional auxiliary substance for granulation or compacting to said solution or suspension.

24. The process of claim 20, wherein said converting comprises drying and compacting.

25. The process of claim 20, wherein said converting comprises spray drying.

26. The process of claim 20, wherein said converting comprises spray drying and granulation.

27. The process of claim 20, wherein said converting comprises spray drying and build-up granulation.

* * * * *